United States Patent
Ni et al.

(10) Patent No.: US 9,938,227 B2
(45) Date of Patent: *Apr. 10, 2018

(54) METHOD FOR PREPARING METHYL FORMATE AND COPRODUCING DIMETHYL ETHER

(71) Applicant: DALIAN INSTITUTE OF CHEMICAL PHYSICS, CHINESE ACADEMY OF SCIENCES, Liaoning Province (CN)

(72) Inventors: Youming Ni, Liaoning Province (CN); Wenliang Zhu, Liaoning Province (CN); Yong Liu, Liaoning Province (CN); Hongchao Liu, Liaoning Province (CN); Zhongmin Liu, Liaoning Province (CN); Lina Li, Liaoning Province (CN); Shiping Liu, Liaoning Province (CN); Hui Zhou, Liaoning Province (CN)

(73) Assignee: DALIAN INSTITUTE OF CHEMICAL PHYSICS, CHINESE ACADEMY OF SCIENCES, Liaoning Province (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/526,868

(22) PCT Filed: Nov. 17, 2014

(86) PCT No.: PCT/CN2014/091291
§ 371 (c)(1),
(2) Date: May 15, 2017

(87) PCT Pub. No.: WO2016/077968
PCT Pub. Date: May 26, 2016

(65) Prior Publication Data
US 2017/0320807 A1    Nov. 9, 2017

(51) Int. Cl.
| | |
|---|---|
| *C07C 69/00* | (2006.01) |
| *C07C 67/39* | (2006.01) |
| *C07C 67/00* | (2006.01) |
| *C07C 69/06* | (2006.01) |
| *C07C 41/50* | (2006.01) |
| *C07C 43/04* | (2006.01) |
| *C07C 43/30* | (2006.01) |
| *B01J 39/05* | (2017.01) |
| *B01J 29/08* | (2006.01) |
| *B01J 29/18* | (2006.01) |
| *B01J 29/40* | (2006.01) |
| *B01J 29/65* | (2006.01) |
| *B01J 29/70* | (2006.01) |
| *B01J 31/10* | (2006.01) |
| *B01J 39/20* | (2006.01) |
| *C07C 41/18* | (2006.01) |

(52) U.S. Cl.
CPC ............ *C07C 67/39* (2013.01); *B01J 29/084* (2013.01); *B01J 29/18* (2013.01); *B01J 29/40* (2013.01); *B01J 29/65* (2013.01); *B01J 29/7007* (2013.01); *B01J 29/7038* (2013.01); *B01J 31/10* (2013.01); *B01J 39/05* (2017.01); *B01J 39/20* (2013.01); *C07C 41/18* (2013.01); *C07C 41/50* (2013.01); *C07C 43/04* (2013.01); *C07C 43/30* (2013.01); *C07C 67/00* (2013.01); *C07C 69/06* (2013.01); *B01J 2231/50* (2013.01); *B01J 2231/70* (2013.01)

(58) Field of Classification Search
CPC B01J 29/7038; B01J 2231/50; B01J 2231/70; B01J 29/084; B01J 29/18; B01J 29/40; B01J 29/65; B01J 29/7007; B01J 31/10; B01J 39/05; B01J 39/20; B01J 31/06; B01J 8/02; C07C 41/50; C07C 69/06; C07C 41/18; C07C 43/04; C07C 43/30; C07C 67/00; C07C 67/39; C07C 41/01; C07C 43/043; C07C 67/36; C07C 67/48; Y02P 20/582

See application file for complete search history.

(56) References Cited

U.S. PATENT DOCUMENTS 6,015,875 A * 1/2000 Smith, Jr. .............. C08G 4/00
203/14

* cited by examiner

*Primary Examiner* — Yevgeny Valenrod
*Assistant Examiner* — Blaine G Doletski
(74) *Attorney, Agent, or Firm* — Nath, Goldberg & Meyer; Tanya E. Harkins; Stanley N. Protigal

(57) ABSTRACT

Method for preparing methyl formate and coproducing dimethyl ether by reacting a formaldehyde and methanol raw material (molar ratio range of 1:4 to 1:0.05) in a First Reaction Region at ranges from 50° C. to 100° C. with Catalyst A resulting in post-reaction material separated into Constituent I. Reacting Constituent I in a Second Reaction Region at ranges from 50° C. to 200° C. and from 0.1 MPa to 10 MPa with Catalyst B resulting in post-reaction material, which is separated into methyl formate, dimethyl ether and Constituent II. At least 1% of dimethyl ether is product, and recycling the rest to the First Reaction Region. Constituent II is recycled to the Second Reaction Region. Each component is gaseous phase and/or liquid phase, independently. The method shows long catalyst life, mild reaction condition, high utilization ratio of raw materials, continuous production and large scale industrial application potential.

10 Claims, 2 Drawing Sheets

METHOD FOR PREPARING METHYL FORMATE AND COPRODUCING DIMETHYL ETHER

This is a National Phase Application filed under 35 U.S.C. 371 as a national stage of PCT/CN2014/091291, filed Nov. 17, 2014, the content of which is hereby incorporated by reference in its entirety.

TECHNICAL FIELD

The present application belongs to the technical field of chemistry and chemical technology, and specifically relates to a method for preparing methyl formate and coproducing dimethyl ether.

BACKGROUND

In C1 chemistry, following methane chemistry, synthesis gas chemistry and methanol chemistry, methyl formate has been developed as a new starting material of C1 chemicals and constitutional unit gradually, because it can be economically and effective produced in large scale, and it can be used in making numerous downstream products, etc. Using methyl formate as a starting material, numerous chemical products of C1 chemistry can be prepared, such as formic acid, acetic acid, glycol, methyl propionate, methyl acrylate, methyl glycolate, N-formylmorpholine, N-methylformamide, N,N-dimethyl formamide and the like.

In the present technology for preparing methyl formate, there are defects including high impurity sensitivity, strict requirement for the purity of raw materials, complex production process, high energy consumption, high investment, hard use of by-byproducts. In view of the above reasons, the yield of single production equipment is generally less than 0.1 million tons each year, making it hard to form scale effect. It will bring important economic vale if methyl formate can be produce under mild conditions by a simple process, using methanol and formaldehyde which are cheap and available bulks chemicals.

DISCLOSURE

An object of the present application is to provide a method for preparing methyl formate and coproducing dimethyl ether, which at least contains the steps as follows:
a) introducing a raw material containing formaldehyde and methanol into a First Reaction Region and contacting with a Catalyst A to react, and separating the post-reaction material to obtain Constituent I;
b) introducing the Constituent I obtained in step a) into a Second Reaction Region and contacting with a Catalyst B to react, and separating the post-reaction material to obtain Constituent II, dimethyl ether and product methyl formate;
c) taking at least 1% of dimethyl ether obtained in step b) as product, and recycling the rest of dimethyl ether obtained in step b) to the First Reaction Region and recycling Constituent II to the Second Reaction Region;
wherein in step a), the reaction temperature of the First Reaction Region ranges from 50° C. to 100° C.;
in said raw material, the molar ratio range of formaldehyde to methanol (formaldehyde:methanol) is from 1:4 to 1:0.05, and the molar of formaldehyde and methanol are calculated according to the molar of carbon atoms contained in formaldehyde and methanol, respectively; the weight hourly space velocity of formaldehyde in the raw material ranges from 0.01 $h^{-1}$ to 15.0 $h^{-1}$;
wherein in step b), the reaction temperature of the Second Reaction Region ranges from 50° C. to 200° C. and the reaction pressure ranges from 0.1 MPa to 10 MPa;
wherein each component in the First Reaction Region and the Second Reaction Region is gaseous phase and/or liquid phase, independently.

As a preferred embodiment, said raw material in step a) is composed of methanol and formaldehyde.

Said Constituent I mainly contain methylal which is produced in the First Reaction Region, and Constituent II mainly contain methylal which is unreacted in the Second Reaction Region.

Methylal ($CH_3O$—$CH_2$—$OCH_3$) can be produced by reaction of formaldehyde ($CH_2O$), dimethyl ether ($CH_3OCH_3$) and methanol ($CH_3OH$). Methyl formate ($HCOOCH_3$) and dimethyl ether can be produced by disproportionation reaction of methylal. Combining the two reactions, it is achieved that methyl formate and dimethyl ether are produced using formaldehyde and methanol as a raw material.

The reactions occurring in the First Reaction Region include the condensation reaction of formaldehyde and methanol as shown in Equation (1) and the condensation reaction of formaldehyde and dimethyl ether as shown in Equation (2). Said Constituent I contain methylal ($CH_3O$—$CH_2$—$OCH_3$) from the above-mentioned condensation reaction products.

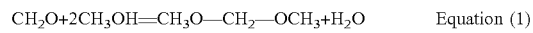

$$CH_2O+2CH_3OH = CH_3O\text{—}CH_2\text{—}OCH_3+H_2O \quad \text{Equation (1)}$$

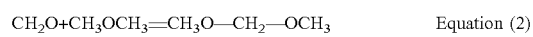

$$CH_2O+CH_3OCH_3 = CH_3O\text{—}CH_2\text{—}OCH_3 \quad \text{Equation (2)}$$

The reactions occurring in the Second Reaction Region include the disproportionation reaction of methylal to produce methyl formate and dimethyl ether as shown in Equation (3).

$$2CH_3O\text{—}CH_2\text{—}OCH_3 = 2CH_3OCH_3+HCOOCH_3 \quad \text{Equation (3)}$$

The overall reaction of the above-mentioned reactions is that methyl formate and dimethyl ether are produced using formaldehyde and methanol as a raw material, as shown in Equation (4).

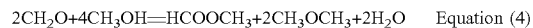

$$2CH_2O+4CH_3OH = HCOOCH_3+2CH_3OCH_3+2H_2O \quad \text{Equation (4)}$$

As an embodiment, all of dimethyl ether produced in the Second Reaction Region is taken as a product. As an embodiment, parts of dimethyl ether produced in the Second Reaction Region are taken as a product, and rest of dimethyl ether produced in the Second Reaction Region is recycled to the First Reaction Region to continue the condensation reaction with formaldehyde. The raw materials are adequately used and the usage amount of methanol is decreased. The ratio of methyl formate to dimethyl ether in the product can be controlled by adjusting the recycle proportion of dimethyl ether, according to the needs of different production. The product composition can be adjusted timely according to the change of market price and supply and demand situation of methyl formate and dimethyl ether, to gain a better economic benefit.

The disproportionation reaction of methylal is an endothermic reaction without the risk of temperature runaway. If components in the product after reaction do not react with the impurities in the raw material (like water), the mole ratio of dimethyl ether to methyl formate in the product will be 2:1 which is equal to the ratio in Equation. In this process, there are no by-products, and methyl formate is easily separated, and the purity of methyl formate is high.

Preferably, in said raw material, the molar ratio range of formaldehyde to methanol (formaldehyde:methanol) is from 1:2.2 to 1:2, and the molar of formaldehyde and methanol are calculated according to the molar of carbon atoms contained in formaldehyde and methanol, respectively. More preferably, in said raw material, the molar ratio of formaldehyde to methanol (formaldehyde:methanol) is 1:2, and the molar of formaldehyde and methanol are calculated according to the molar of carbon atoms contained in formaldehyde and methanol, respectively.

In step a), the process of introducing said raw material into the First Reaction Region and contacting with the Catalyst A to react, and separating the post-reaction material can be that said raw material contacts with the Catalyst A to react firstly, and then the post-reaction material is introduced into a separation system to be separated; or the process also can be that the reaction and separation in the same device, i.e. the process is a catalytic distillation process. In catalytic distillation device, one or more catalyst beds are situated in one or more zones of the catalytic distillation tower, simultaneously acting as fixed-bed reactor and rectifying tower plates/packing, to save the investment of equipment. The reaction exotherm can be used to provide heat for distillation separation, decreasing thermal load of reboiler and reducing energy consumption. The post-reaction material is directly separated in the catalytic distillation tower, the products leave from catalytic distillation system and the unreacted raw materials keep on contacting with the catalyst beds to react. Thus, the purposes including reaction, separation and recycling the unreacted raw materials to the First Reaction Region can be realized at the same time.

A skilled person of the art can obtain methylal with different purities by adjusting the process conditions of said catalytic distillation device, such as temperature, pressure, ratio of the raw materials, reflux ratio, feeding location and the like. Preferably, in step a), the Catalyst A is loaded in a distillation reaction device; and in the distillation reaction device, the reflux ratio ranges from 0.5 to 10; and the upper limit of temperature range is selected from 90° C. or 100° C. and the lower limit of temperature range is selected from 50° C. or 60° C.; and the upper limit of weight hourly space velocity range of formaldehyde in the raw material is selected from 3.0 h$^{-1}$ or 15 h$^{-1}$, and the lower limit of weight hourly space velocity range of formaldehyde in the raw material is selected from 0.01 h$^{-1}$ or 0.5 h$^{-1}$. More preferably, in step a), the Catalyst A is loaded in a distillation reaction device; and in the distillation reaction device, reflux ratio ranges from 0.5 to 10, and temperature ranges from 60° C. to 90° C.; the weight hourly space velocity of formaldehyde in the raw material ranges from 0.5 h$^{-1}$ to 3.0 h$^{-1}$. Said First Reaction Region is composed of one or more catalytic distillation devices.

Preferably, in step c), at least 5% of dimethyl ether obtained in step b) is taken as product, and recycling the rest of dimethyl ether obtained in step b) to the First Reaction Region.

More preferably, in step c), at least 10% of dimethyl ether obtained in step b) is taken as product, and recycling the rest of dimethyl ether obtained in step b) to the First Reaction Region.

Further preferably, in step c), at least 50% of dimethyl ether obtained in step b) is taken as product, and recycling the rest of dimethyl ether obtained in step b) to the First Reaction Region.

Further preferably, in step c), at least 90% of dimethyl ether obtained in step b) is taken as product, and recycling the rest of dimethyl ether obtained in step b) to the First Reaction Region.

Further preferably, in step c), at least 95% of dimethyl ether obtained in step b) is taken as product, and recycling the rest of dimethyl ether obtained in step b) to the First Reaction Region.

Preferably, in step a), the Catalyst A is at least one selected from a strong acidic cation exchanger resin.

More preferably, in step a), the Catalyst A is a sulfonated styrene-divinylbenzene copolymer resin with strong acid and macro-pores, which is obtained by sulfonating styrene-divinylbenzene copolymer using sulfuric acid.

Preferably, in step b), the upper limit of reaction temperature range in the Second Reaction Region is selected from 150° C. or 200° C., the lower limit of reaction temperature range in the Second Reaction Region is selected from 50° C. or 60° C.; the upper limit of reaction pressure range is selected from 2 MPa or 10 MPa, and the lower limit of reaction pressure range is 0.1 MPa. More preferably, the reaction temperature of the Second Reaction Region ranges from 60° C. to 150° C. and the reaction pressure ranges from 0.1 MPa to 2 MPa.

Preferably, in step b), the Catalyst B is at least one selected from acid molecular sieves or strong acidic cation exchanger resins.

Preferably, the structural type of said acid molecular sieves is MWW, FER, MFI, MOR, FAU or BEA. More preferably, the ratio of silicate to aluminium Si/Al of said acid molecular sieves ranges from 3:1 to 150:1.

More preferably, in step b), the Catalyst B is at least one selected from H-type MCM-22 zeolite, H-type ZSM-5 zeolite, H-type Y zeolite, H-type BETA zeolite, H-type ferrierite, H-type mordenite or perfluorosulfonate resin (abbreviated as Nafion-H).

According to the common general knowledge of the art, H-type molecular sieves or zeolites are normally obtained from molecular sieves or zeolites by calcination after exchange with ammonium ions.

In the present application, multiple reactor types are suitable for said Second Reaction Region. A skilled person of the art can choose different reactor types to realize the purpose and technical effect. Preferably, said Second Reaction Region contains at least one selected from fixed-bed reactor, tank reactor, moving-bed reactor or fluid bed reactor. Because the Catalyst B in the Second Reaction Region has an outstanding long-life advantage and fixed-bed reactor has greater advantages in investment costs, engineering design, producing operation, the fixed-bed reactor is a more preferable embodiment. Further preferably, said Second Reaction Region is composed of a fixed-bed reactor; or the Second Reaction Region is composed of a number of fixed-bed reactors in parallel and/or in series.

The advantages of the present application include but not limit to:

1) The method provided in the present application has advantages of low-cost, environment-friendly, high production safety. The raw materials are low cost formaldehyde aqueous solution and methanol aqueous solution. High pure methyl formate and dimethyl ether are produced by two-steps method. In the disproportionation reaction of methylal, the process is simple, and the reaction conditions are mild, and an excellent result can be got at lower reaction temperature and pressure. The disproportionation reaction of methylal is an endothermic reaction without the risk of temperature runaway, whose process safety is high. The catalyst is stable and suitable for continuous production in large scale. The cost and energy consumption of product separation are low, which makes it easy to obtain high pure methyl formate and dimethyl ether. Comparing with the process of methanol carbonylation, it avoids using carbon monoxide in raw materials, expensive gas making equipment, transformation equipment and gas separation equipment.

2) In the method provided in the present application, Catalyst B in the Second Reaction Region has a long catalytic life and an excellent catalytic performance.

3) Using the method provided in the present application, the ratio of methyl formate to dimethyl ether in the product can be adjusted flexibly according to the change of market price and supply and demand situation.

4) Using the method provided in the present application, the utilization rate of raw materials is high.

5) The method provided in the present application is not only suitable for large-scale integrated production, but also for small-scale production with low investment in small and medium-sized enterprises. It is very flexible and there are few restrictions on area and facilities.

The foregoing is detailed description of the present invention, while the present invention is not limited to the detailed description of the embodiments. Those skilled in the art can understand that various modifications and other changes may be made from the scope of the invention.

DETAILED DESCRIPTION OF THE EMBODIMENTS

Figure 1:
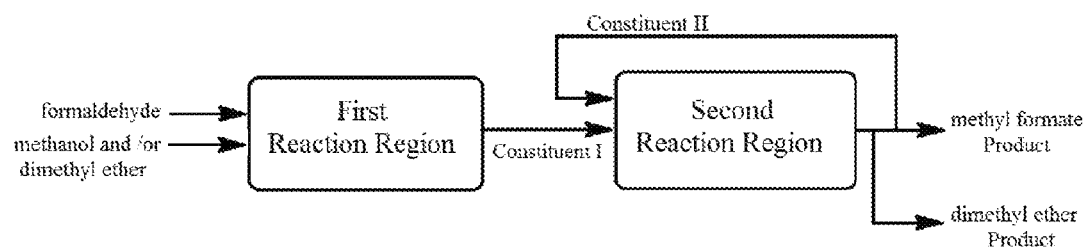
FIG. 1 is a technological flow sheet of an embodiment of the present application.

As an embodiment of the present application, the technological flow sheet is shown in FIG. 1. The raw material containing formaldehyde and methanol is introduced into a First Reaction Region, and after reacting and separating, the unreacted raw materials continue reacting in the First Reaction Region; and the Constituent I (mainly methylal), which is obtained by separating the post-reaction material of the First Reaction Region, is introduced into a Second Reaction Region; and the post-reaction material of the Second Reaction Region is separated to obtain dimethyl ether, methyl formate and Constituent II (mainly methylal); and dimethyl ether and methyl formate are stored as the products, respectively; and the Constituent II (mainly methylal) is recycled to the Second Reaction Region.

Figure 2:
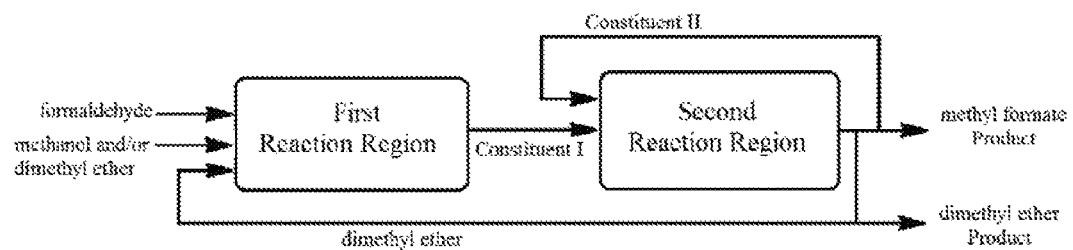
FIG. 2 is a technological flow sheet of an embodiment of the present application.

As other embodiment of the present application, the technological flow sheet is shown in FIG. 2. The raw material containing formaldehyde and methanol is introduced into a First Reaction Region, and after reacting and separating, the unreacted raw materials continue reacting in the First Reaction Region; and the Constituent I (mainly methylal), which is obtained by separating the post-reaction material of the First Reaction Region, is introduced into a Second Reaction Region; and the post-reaction material of the Second Reaction Region is separated to obtain dimethyl ether, methyl formate and Constituent II (mainly methylal); and part of dimethyl ether is stored as the product and the rest of dimethyl ether is recycled to the First Reaction Region; and methyl formate is stored as the product; and the Constituent II (mainly methylal) is recycled to the Second Reaction Region.

The present application will be further described by combining with Examples. It should be understand that these Examples are only used to illustrate the present application and not to limit the scope of the present application.

Without special explanation, the reagents and catalysts in the Examples are from commercial purchase.

Amberlyst-15 Resin is a sulfonated styrene-divinylbenzene copolymer resin with strong acid and macro-pores, purchased from ROHM HRRS Company.

DNW Resin and D005 Resin are sulfonated styrene-divinylbenzene copolymer resin with strong acid and macro-pores, purchased from Dandong Mingzhu Special Resin Limited Company.

D006 Resin and D007 Resin are sulfonated styrene-divinylbenzene copolymer resin with strong acid and macro-pores, purchased from Cary environmental technology co., LTD.

In the Examples, analysis method and calculation method of percent conversion and selectivity are as follows:

The components of gas/liquid phase are auto analyzed using Agilent7890 gas chromatograph with gas autosampler, FID detector and PLOT-Q capillary column.

In the Examples of the present application, the calculation of percent conversion per pass of methylal and selectivity per pass of methyl formate and dimethyl ether are based on the carbon mole number.

Percent conversion per pass of methylal=[(the carbon mole number of methylal in the feedstock of Second Reaction Region)−(the carbon mole number of methylal in the discharge of Second Reaction Region)]÷(the carbon mole number of methylal in the feedstock of Second Reaction Region)×(100%)

Selectivity per pass of methyl formate=(the carbon mole number of methyl formate in the discharge of Second Reaction Region)÷[(the carbon mole number of methylal in the feedstock of Second Reaction Region)−(the carbon mole number of methylal in the discharge of Second Reaction Region)]×(100%)

Selectivity per pass of dimethyl ether=(the carbon mole number of dimethyl ether obtained by the conversion of methylal in the discharge of Second Reaction Region)÷[(the carbon mole number of methylal in the feedstock of Second Reaction Region)−(the carbon mole number of methylal in the discharge of Second Reaction Region)]×(100%)

Proportion of the product dimethyl ether=[(the carbon mole number of dimethyl ether obtained by the conversion of methylal in the Second Reaction Region)−(the carbon mole number of dimethyl ether recycled to the First Reaction Region)]÷(the carbon mole number of dimethyl ether obtained by the conversion of methylal in the Second Reaction Region)×(100%)

In the present application, the carbon mole number is the mole number of carbon atoms in each component.

The present application will be described in details by Examples, but the present application is not limited to these Examples.

Example 1

Figure 3:
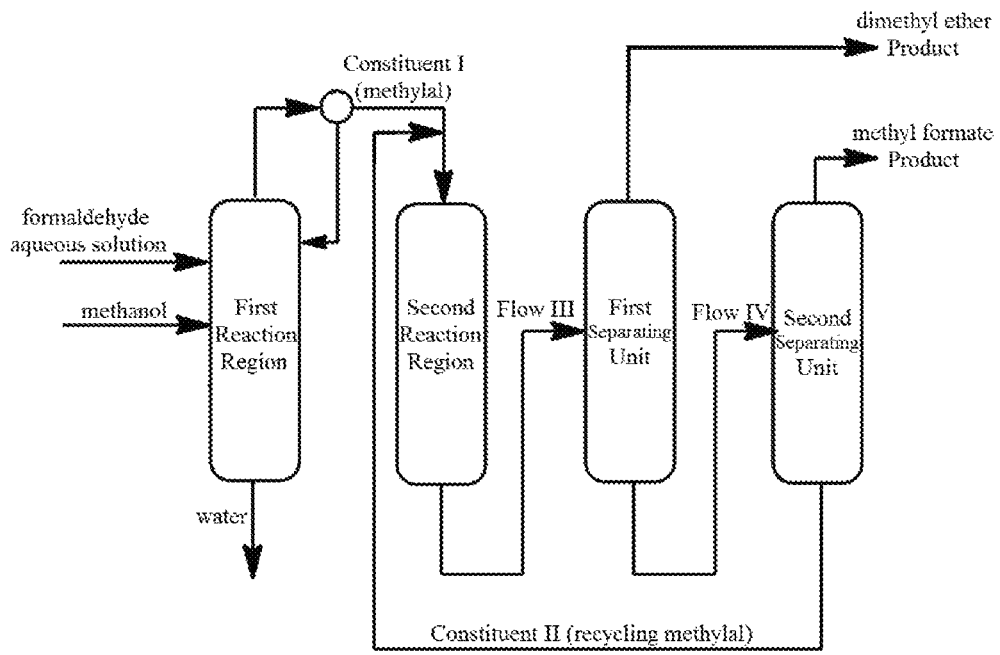
FIG. 3 is the technological flow sheet for preparing methyl formate and coproducing dimethyl ether in Example 1.

The technological process for preparing methyl formate and coproducing dimethyl ether:

As a typical embodiment of the present application, the technological flow sheet for preparing methyl formate and coproducing dimethyl ether was shown in FIG. 3. A catalytic distillation tower was used in the First Reaction Region to carry out the condensation reaction of formaldehyde and methanol for preparing methylal; and a fixed-bed reactor was used in the Second Reaction Region to carry out the disproportionated reaction of methylal; and a First Separating Unit was used to separate dimethyl ether from the products of disproportionated reaction of methylal; and a Second Separating Unit was used to separate methyl formate and the unreacted raw materials from the products of disproportionated reaction of methylal.

Specifically, the raw material contained formaldehyde aqueous solution and methanol; the raw material was introduced into the catalytic distillation tower of the First Reaction Region; and after the raw material contacts with the catalyst bed, the constituent containing formaldehyde, methanol and dimethyl ether was returned to the catalyst bed in the catalytic distillation tower to continue reacting, and the Constituent I mainly was methylal of the condensation reaction product which was obtained from tower top, and water of the condensation reaction product was obtained from tower bottom. The Constituent I was introduced into the Second Reaction Region for disproportionated reaction of methylal. The Flow III of disproportionated reaction product was introduced into the First Separating Unit to obtain the product dimethyl ether and Flow IV by separating; and the Flow IV was introduced into the Second Separating Unit to obtain the product methyl formate and Constituent II by separating; and the Constituent II mainly was methylal used to be recycled; and the Constituent II was recycled to the Second Reaction Region to continue reacting. Using the above-mentioned process, the product, in which the carbon molar number ratio of methyl formate to dimethyl ether was approximate 1:2, was obtained using formaldehyde and methanol as raw materials.

In the First Reaction Region, the process of the condensation reaction of formaldehyde and methanol for preparing methylal was according to the following steps:

In a stainless steel catalytic distillation tower with an internal diameter of 30 mm and a height of 1800 mm, 500 g of Amberlyst-15 Resin catalyst packed by stainless steel cloth was loaded at lower end of the tower as the reaction zone with a height of 1200 mm; and the Φ4 mm×4 mm of stainless steel wire was loaded at upper end of the tower as the packing of rectification zone with a height of 600 mm. The reflux ratio of the tower top condenser could be controlled. The volume of the tower bottom reboiler was 3000 ml. The heater wires were winded around the outer wall of reaction zone to make temperature from top down equably increase from 60° C. to 90° C. 37% of formaldehyde aqueous solution, 96% of methanol aqueous solution and dimethyl ether from the Second Reaction Region in sequence were introduced into three feed inlets of the catalytic distillation tower from top down. The ratio of formaldehyde to methanol was listed in Table 1. The proportion of the product dimethyl ether to the total dimethyl ether in the discharge of Second Reaction Region was listed in Table 1, and the rest of dimethyl ether was recycled to the catalytic distillation tower of the First Reaction Region. Gradually adjusting the power of reboiler and the reflux ratio, until more than 99.5% of methylal was obtained from the tower top.

In the Second Reaction Region, the process of the disproportionated reaction of methylal for preparing methyl formate and coproducing dimethyl ether is according to the following steps:

300 g of H-type MCM-22 with the atom ratio of Si/Al=40:1 was calcinated in air at 550° C. for 5 hours in Muffle furnace, and then part of the powder sample was taken, pressed, crushed and sieved to 20-40 mesh sample used for the catalytic performance testing. 200 g of the above-mentioned H-type MCM-22 sample was weighed and loaded into a stainless steel reaction tube with an internal diameter of 30 mm. The sample was activated at 550° C. for 4 hour under nitrogen gas at atmospheric pressure and the temperature was reduced to 90° C., and then the methylal obtained from the First Reaction Region was introduced and the pressure was 0.1 MPa. The reaction products were analyzed by a gas chromatograph. After the reaction being stable, the percent conversion per pass of methylal and the selectivity per pass of methyl formate were calculated. The results were shown in Table 1. The products of the Second Reaction Region were separated by two-stage rectified to obtain methyl formate, dimethyl ether and the unreacted methylal; wherein methyl formate and dimethyl ether were stored as the products respectively and the unreacted methylal was recycled to the Second Reaction Region.

Combining the two reactions, it was achieved that more than 99.99% of methyl formate and dimethyl ether was obtained using 37% of formaldehyde aqueous solution and 96% of methanol aqueous solution as the raw materials.

Example 2

Figure 4:
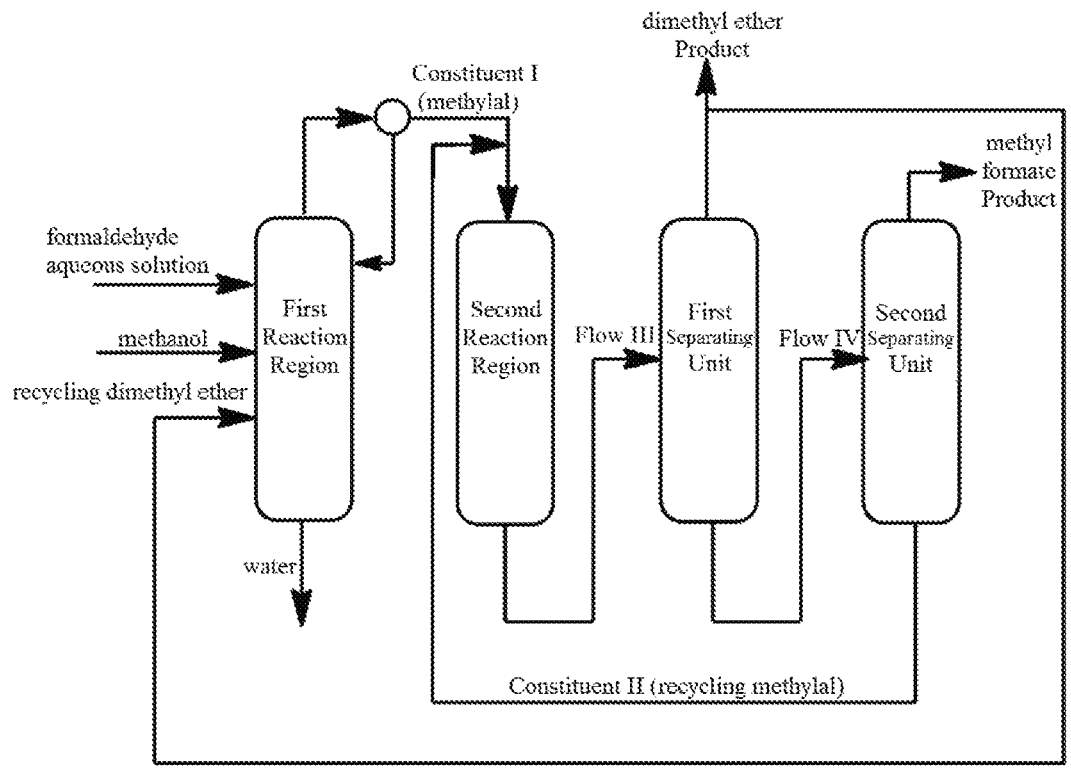
FIG. 4 is the technological flow sheet for preparing methyl formate and coproducing dimethyl ether in Example 2.

The technological process for preparing methyl formate and coproducing dimethyl ether:

As a typical embodiment of the present application, the technological flow sheet for preparing methyl formate and coproducing dimethyl ether was shown in FIG. 4. A catalytic distillation tower was used in the First Reaction Region to carry out the condensation reaction of formaldehyde, methanol and dimethyl ether for preparing methylal; and a fixed-bed reactor was used in the Second Reaction Region to carry out the disproportionated reaction of methylal; and a First Separating Unit was used to separate dimethyl ether from the products of disproportionated reaction of methylal; and a Second Separating Unit was used to separate methyl formate and the unreacted raw materials from the products of disproportionated reaction of methylal.

Specifically, the raw material contained fresh formaldehyde aqueous solution, fresh methanol and recycling dimethyl ether; the raw material was introduced into the catalytic distillation tower of the First Reaction Region; and after the raw material contacts with the catalyst bed, the constituent containing formaldehyde, methanol and dimethyl ether was returned to the catalyst bed in the catalytic distillation tower to continue reacting, and the Constituent I mainly was methylal of the condensation reaction product which was obtained from tower top, and water of the condensation reaction product was obtained from tower bottom. The Constituent I was introduced into the Second Reaction Region for disproportionated reaction of methylal. The Flow III of disproportionated reaction product was introduced into the First Separating Unit to obtain dimethyl ether and Flow IV by separating; and part of dimethyl ether was as the product and the rest of dimethyl ether was recycled to the First Reaction Region. The Flow IV was introduced into the Second Separating Unit to obtain the product methyl formate and Constituent II by separating; and the Constituent II mainly was methylal used to be recycled; and the Constituent II was recycled to the Second Reaction Region to continue reacting. Using the above-mentioned process, it was realized that the product of methyl formate and dimethyl ether was prepared using formaldehyde and methanol as raw materials. And the ratio of methyl formate to dimethyl ether in the product could be controlled by adjusting the ration of the product dimethyl ether to the recycling dimethyl ether. The proportion of the recycling dimethyl ether to the total dimethyl ether obtained in the Second Reaction Region was higher, and the proportion of the product dimethyl ether was lower, the proportion of methyl formate in the product was higher.

The Catalyst A in the First Reaction Region, the Catalyst B in the Second Reaction Region, the proportion of the product dimethyl ether to the total dimethyl ether obtained in the Second Reaction Region, the raw material ratio, the weight hourly space velocity (WHSV) of formaldehyde in the raw material, the reaction temperature in the Second Reaction Region, the reaction pressure in the Second Reaction Region were shown in Table 1. The rest experimental procedure was same as Example 1. The results were shown in Table 1.

Example 3

The Catalyst A in the First Reaction Region, the Catalyst B in the Second Reaction Region, the proportion of the product dimethyl ether to the total dimethyl ether obtained in the Second Reaction Region, the raw material ratio, the weight hourly space velocity (WHSV) of formaldehyde in the raw material, the reaction temperature in the Second Reaction Region, the reaction pressure in the Second Reaction Region were shown in Table 1. The rest experimental procedure was same as Example 1. The results were shown in Table 1.

Examples 4 to 6

The Catalyst A in the First Reaction Region, the Catalyst B in the Second Reaction Region, the proportion of the product dimethyl ether to the total dimethyl ether obtained in the Second Reaction Region, the raw material ratio, the weight hourly space velocity (WHSV) of formaldehyde in the raw material, the reaction temperature in the Second Reaction Region, the reaction pressure in the Second Reaction Region were shown in Table 1. The rest experimental procedure was same as Example 2. The results were shown in Table 1.

Examples 7 and 8

The Catalyst B in the Second Reaction Region was shown in Table 1. 200 g of the 20-40 mesh samples were weighed and loaded into a stainless steel reaction tube with an internal diameter of 30 mm. Before reacting, the samples were activated at 100° C. for 1 hour under nitrogen gas at atmospheric pressure. The Catalyst A in the First Reaction Region, the proportion of the product dimethyl ether to the total dimethyl ether obtained in the Second Reaction Region, the raw material ratio, the weight hourly space velocity (WHSV) of formaldehyde in the raw material in the First Reaction Region, the reaction temperature in the Second Reaction Region, the reaction pressure in the Second Reaction Region were shown in Table 1. The rest experimental procedure was same as Example 1. The results were shown in Table 1.

Example 9

The Second Reaction Region was composed of two fixed-bed reactors in series. Each fixed-bed reactor was loaded by 100 g of the Catalyst B. Other reaction conditions were shown in Table 1. The rest experimental procedure was same as Example 7. The results were shown in Table 1.

Example 10

The Second Reaction Region was composed of two fixed-bed reactors in parallel. Each fixed-bed reactor was loaded by 100 g of the Catalyst B. Other reaction conditions were shown in Table 1. The rest experimental procedure was same as Example 7. The results were shown in Table 1.

TABLE 1

Reaction conditions and results in Examples 1 to 10

| Example | Catalyst A in the First Reaction | Catalyst B in the Second Reaction | Molar ratio of carbons in raw material of the First Reaction Region ($CH_2O:CH_3OH$) | WHSV of $CH_2O$ in raw material of the First Reaction Region ($h^{-1}$) | Reaction temperature in the Second Reaction (° C.) | Reaction pressure in the Second Reaction (MPa) | Percent conversion per pass of methylal (%) | Selectivity per pass of methyl formate (%) | Selectivity per pass of dimethyl ether (%) | Proportion of the product dimethyl ether (%) | Catalyst life per pass in the Second Reaction (day) |
|---|---|---|---|---|---|---|---|---|---|---|---|
| 1 | Amberlyst-15 Resin | H-type MCM-22 (Si/Al = 40) | 1:2 | 3.0 | 90 | 0.1 | 78.4 | 33.2 | 66.3 | 100 | 150 |
| 2 | Amberlyst-15 Resin | H-type ferrierite (Si/Al = 10) | 1:1.8 | 0.5 | 150 | 2 | 94.2 | 33.2 | 66.2 | 90 | 160 |
| 3 | DNW Resin | H-type ZSM-5 (Si/Al = 150) | 1:4 | 0.01 | 60 | 1 | 41.8 | 33.0 | 66.4 | 100 | 330 |
| 4 | D005 Resin | H-type mordenite (Si/Al = 3/1) | 1:0.05 | 15 | 200 | 10 | 68.2 | 33.1 | 66.5 | 1 | 110 |
| 5 | D006 | H-type Y | 1:0.2 | 6 | 50 | 5 | 39.2 | 33.1 | 66.4 | 10 | 150 |

TABLE 1-continued

Reaction conditions and results in Examples 1 to 10

| Example | Catalyst A in the First Reaction | Catalyst B in the Second Reaction | Molar ratio of carbons in raw material of the First Reaction Region (CH$_2$O:CH$_3$OH) | WHSV of CH$_2$O in raw material of the First Reaction Region (h$^{-1}$) | Reaction temperature in the Second Reaction (° C.) | Reaction pressure in the Second Reaction (MPa) | Percent conversion per pass of methylal (%) | Selectivity per pass of methyl formate (%) | Selectivity per pass of dimethyl ether (%) | Proportion of the product dimethyl ether (%) | Catalyst life per pass in the Second Reaction (day) |
|---|---|---|---|---|---|---|---|---|---|---|---|
| 6 | Resin D007 resin | (Si/Al = 20) H-type BETA (Si/Al = 15) | 1:1 | 1.5 | 120 | 0.5 | 77.1 | 33.0 | 66.5 | 50 | 190 |
| 7 | Amberlyst-15 Resin | Nafion-H Resin | 1:2 | 1.0 | 100 | 0.3 | 73.5 | 33.2 | 66.4 | 100 | 210 |
| 8 | Amberlyst-15 Resin | Amberlyst-15 Resin | 1:2 | 1.0 | 100 | 0.3 | 38.8 | 33.0 | 66.4 | 100 | 220 |
| 9 | Amberlyst-15 Resin | Nafion-H Resin | 1:2 | 1.0 | 100 | 0.3 | 74.3 | 33.2 | 66.3 | 100 | 205 |
| 10 | Amberlyst-15 Resin | Nafion-H Resin | 1:2 | 1.0 | 100 | 0.3 | 73.5 | 33.0 | 66.4 | 100 | 220 |

Annotation 1: in Table 1, Amberlyst-15 Resin was purchased from ROHM HRRS Company. DNW Resin and D005 Resin were purchased from Dandong Mingzhu Special Resin Limited Company. D006 Resin and D007 Resin were purchased from Cary environmental technology co., LTD. Nafion-H was purchased from DuPont Company (USA).
Annotation 2: the condition parameters in Table 1 were steady-state data.

The foregoing is detailed description of the present application for the sake of enabling those skilled in the art to understand the present application, however, it can be conceived that other variations and modifications can be made without departing from the scope covered by the claims of the present application, and all of these variations and modifications fall into the scope of protection of the present application.

The invention claimed is:

1. A method for preparing methyl formate and coproducing dimethyl ether, which at least contains the steps as follows:
   a) introducing a raw material containing formaldehyde and methanol into a First Reaction Region and contacting with a Catalyst A to react, and separating the post-reaction material to obtain Constituent I;
   b) introducing the Constituent I obtained in step a) into a Second Reaction Region and contacting with a Catalyst B to react, and separating the post-reaction material to obtain Constituent II, dimethyl ether and the product methyl formate;
   c) taking at least 1% of dimethyl ether obtained in step b) as product, and recycling the rest of dimethyl ether obtained in step b) to the First Reaction Region and recycling the Constituent II to the Second Reaction Region;
   wherein in step a), the reaction temperature of the First Reaction Region ranges from 50° C. to 100° C.;
   in said raw material, the molar ratio range of formaldehyde to methanol is from 1:4 to 1:0.05, and the molar of formaldehyde and methanol are calculated according to the molar of carbon atoms contained in formaldehyde and methanol, respectively; the weight hourly space velocity of formaldehyde in the raw material ranges from 0.01 h$^{-1}$ to 15.0 h$^{-1}$;
   wherein in step b), the reaction temperature of the Second Reaction Region ranges from 50° C. to 200° C. and the reaction pressure ranges from 0.1 MPa to 10 MPa;
   wherein each component in the First Reaction Region and the Second Reaction Region is gaseous phase and/or liquid phase, independently.

2. A method for preparing methyl formate and coproducing dimethyl ether according to claim 1, wherein in step a), the Catalyst A is loaded in a distillation reaction device; and in the distillation reaction device, the reflux ratio ranges from 0.5 to 10, and the temperature ranges from 60° C. to 90° C.; the weight hourly space velocity of formaldehyde in the raw material ranges from 0.5 h$^{-1}$ to 3.0 h$^{-1}$.

3. A method for preparing methyl formate and coproducing dimethyl ether according to claim 1, wherein in step c), at least 10% of dimethyl ether obtained in step b) is taken as product, and recycling the rest of dimethyl ether obtained in step b) to the First Reaction Region.

4. A method for preparing methyl formate and coproducing dimethyl ether according to claim 1, wherein in step c), at least 90% of dimethyl ether obtained in step b) is taken as product, and recycling the rest of dimethyl ether obtained in step b) to the First Reaction Region.

5. A method for preparing methyl formate and coproducing dimethyl ether according to claim 1, wherein in step a), the Catalyst A is a strong acidic cation exchanger resin.

6. A method for preparing methyl formate and coproducing dimethyl ether according to claim 1, wherein in step a), the Catalyst A is a sulfonated styrene-divinylbenzene copolymer resin with strong acid and macro-pores.

7. A method for preparing methyl formate and coproducing dimethyl ether according to claim 1, wherein in step b), the reaction temperature of the Second Reaction Region ranges from 60° C. to 150° C. and the reaction pressure ranges from 0.1 MPa to 2 MPa.

8. A method for preparing methyl formate and coproducing dimethyl ether according to claim 1, wherein in step b), the Catalyst B is at least one selected from acid molecular sieves or strong acidic cation exchanger resins.

9. A method for preparing methyl formate and coproducing dimethyl ether according to claim 1, wherein in step b), the Catalyst B is at least one selected from H-type MCM-22 zeolite, H-type ZSM-5 zeolite, H-type Y zeolite, H-type BETA zeolite, H-type ferrierite, H-type mordenite or perfluorosulfonate resin.

10. A method for preparing methyl formate and coproducing dimethyl ether according to claim 1, wherein the Second Reaction Region is composed of a fixed-bed reactor;

or the Second Reaction Region is composed of a number of fixed-bed reactors in parallel and/or in series.

* * * * *